(12) United States Patent
Gray

(10) Patent No.: US 8,216,312 B2
(45) Date of Patent: Jul. 10, 2012

(54) SPINAL INTERBODY SYSTEM AND METHOD

(75) Inventor: Wayne Gray, Pflugerville, TX (US)

(73) Assignee: Zimmer Spine, Inc., Minneapolis, MN (US)

( * ) Notice: Subject to any disclaimer, the term of this patent is extended or adjusted under 35 U.S.C. 154(b) by 744 days.

(21) Appl. No.: 11/756,483

(22) Filed: May 31, 2007

(65) Prior Publication Data

US 2008/0300634 A1    Dec. 4, 2008

(51) Int. Cl.
*A61F 2/44* (2006.01)

(52) U.S. Cl. .................. 623/17.11; 623/17.16; 606/249; 606/280

(58) Field of Classification Search .......... 606/246–254, 606/264–276, 280; 623/17.11–17.16
See application file for complete search history.

(56) References Cited

U.S. PATENT DOCUMENTS

| | | | |
|---|---|---|---|
| 4,768,787 A | 9/1988 | Shira | |
| 4,964,641 A | 10/1990 | Miesch et al. | |
| 5,526,664 A | 6/1996 | Vetter | |
| 5,961,518 A | 10/1999 | Errico et al. | |
| 5,989,250 A | 11/1999 | Wagner et al. | |
| 6,030,250 A | 2/2000 | Sawayanagi et al. | |
| 6,106,557 A | 8/2000 | Robioneck et al. | |
| 6,156,037 A * | 12/2000 | LeHuec et al. | 606/247 |
| 6,235,059 B1 | 5/2001 | Renezech et al. | |
| 6,331,179 B1 | 12/2001 | Freid et al. | |
| 6,454,769 B2 | 9/2002 | Wagner et al. | |
| 6,576,017 B2 | 6/2003 | Foley et al. | |
| 6,736,850 B2 | 5/2004 | Davis | |
| 6,964,664 B2 | 11/2005 | Freid et al. | |
| 7,112,222 B2 | 9/2006 | Fraser et al. | |
| 7,172,627 B2 | 2/2007 | Fiere et al. | |
| 2001/0020185 A1 | 9/2001 | Ray | |
| 2002/0058939 A1 | 5/2002 | Wagner et al. | |
| 2004/0249377 A1 | 12/2004 | Kaes et al. | |
| 2005/0101960 A1* | 5/2005 | Fiere et al. | 606/72 |
| 2005/0159813 A1 | 7/2005 | Molz | |
| 2006/0235409 A1 | 10/2006 | Blain | |
| 2006/0235533 A1 | 10/2006 | Blain | |
| 2008/0161925 A1* | 7/2008 | Brittan et al. | 623/17.16 |

FOREIGN PATENT DOCUMENTS

| | | |
|---|---|---|
| FR | 2727005 | 5/1996 |
| FR | 2815846 | 5/2002 |
| JP | 2001/190579 | 7/2001 |
| WO | WO2004/069106 | 8/2004 |

\* cited by examiner

*Primary Examiner* — Eduardo C Robert
*Assistant Examiner* — Christina Negrelli
(74) *Attorney, Agent, or Firm* — Seager Tufte & Wickhem LLC

(57) ABSTRACT

Embodiments of the present invention provide spinal implant systems and methods. According to one embodiment, a plate attached to one or more vertebrae can prevent expulsion of an interbody device from a disc space. The plate and interbody device can be coupled by an attachment member. According to one embodiment, the attachment member is coupled to the plate and includes a portion inserted in a threaded or non-threaded cavity. Preferably, the coupling between the plate and attachment member allows rotation in three dimensions thereby allowing the plate to rotate relative to the interbody device. This allows the plate to be better positioned for attachment to the spine during an operation.

46 Claims, 16 Drawing Sheets

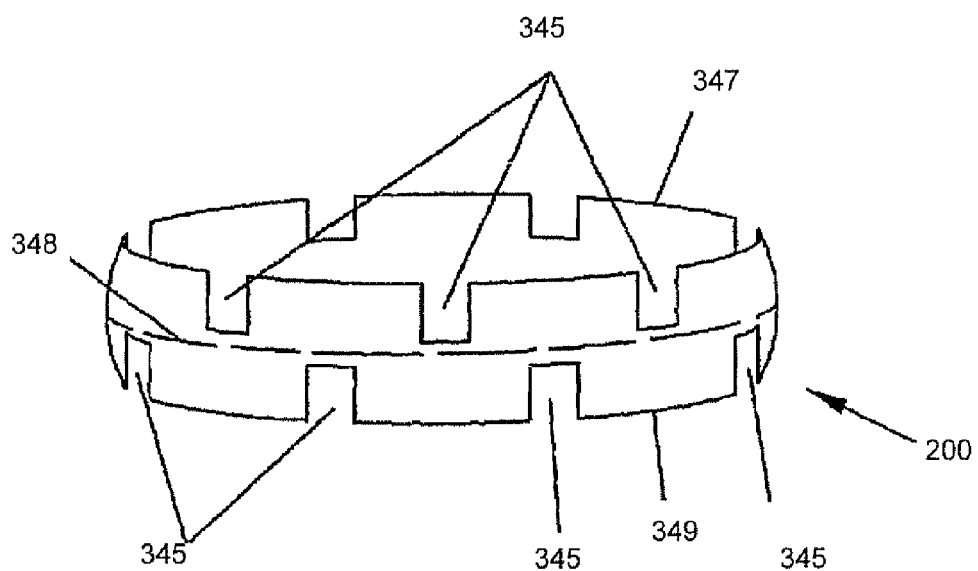
FIGURE 12
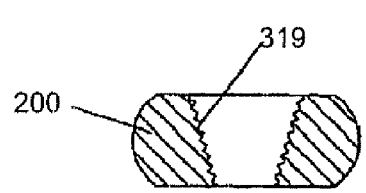 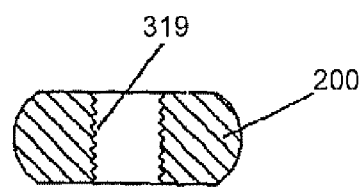
FIGURE 13A    FIGURE 13B
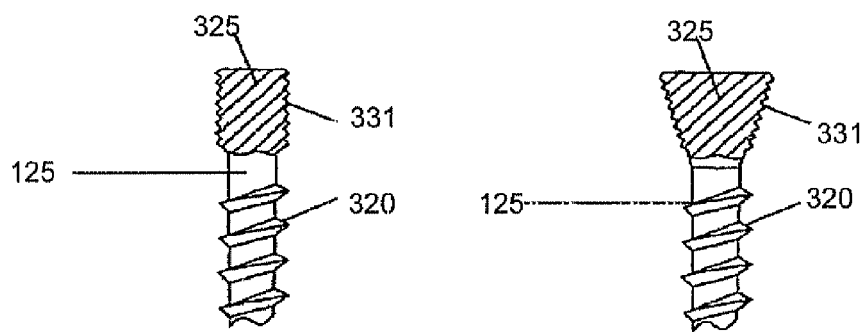
FIGURE 14A    FIGURE 14B

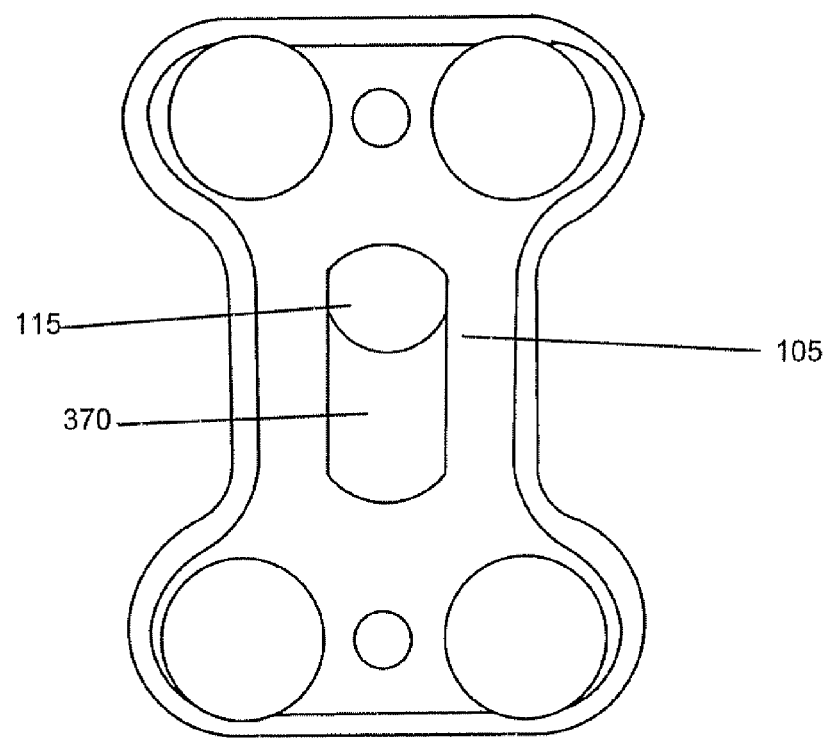
FIGURE 17
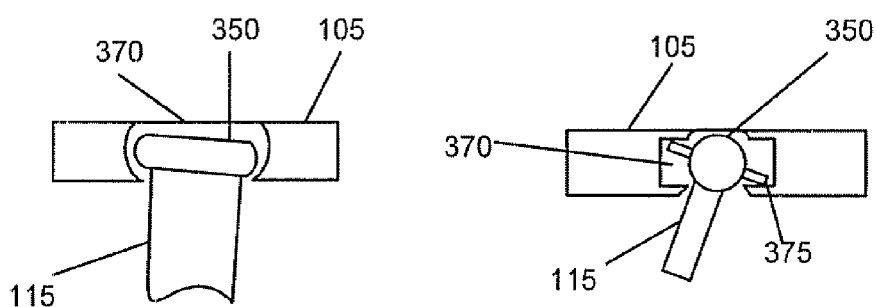
FIGURE 18A
FIGURE 18B

SPINAL INTERBODY SYSTEM AND METHOD

TECHNICAL FIELD OF THE INVENTION

Embodiments of the present invention relate to spinal implants. Even more particularly, embodiments of the present invention relate to interbody devices implanted between vertebrae.

BACKGROUND OF THE INVENTION

A number of maladies afflict the spine, causing severe pain, loss of mobility and decreased quality of life. Some examples of such disorders include degenerative disc disease, scoliosis, spinal deformities and other spinal conditions. Additionally, vertebral fractures and other trauma can cause spinal suffering.

Some conditions can be treated by surgical techniques such as spinal fusion. In spinal fusion, vertebrae are fused together by bone growth to immobilize the vertebrae and reduce pain. In spinal fusion procedures, a small interbody device of plastic, titanium or other biocompatible material is inserted between the vertebrae in place of the natural intervertebral disc. Often a surgeon will perform an anterior procedure to insert the interbody device.

Once the interbody device is in place, a surgeon typically has two options for limiting the movement of the interbody device. According to the first technique, the interbody device is attached to the vertebrae from the back using bone screws. Unfortunately, this requires that the surgeon open the patient on both the anterior and posterior sides. According to the second technique, the surgeon installs a separate rigid plate that spans the vertebrae that need to be immobilized. One problem with this technique is that movement of the interbody device can assert impact forces on the plate causing the bone screws attaching the plate to the spine to back out.

SUMMARY OF THE INVENTION

Embodiments of the present invention provide a spinal implant system and method for spinal interbodies that limit the movement between an interbody and a plate.

One embodiment of the present invention includes a spinal implant comprising a plate for stabilizing the spine, an interbody device defining a cavity opening to a first face and an attachment member coupled to the plate and comprising a first portion inserted in the cavity of the interbody. The attachment member is rotatable about at least three axes relative to the plate.

Another embodiment of the present invention can include a spinal implant comprising a plate for stabilizing the spine, an interbody device having a counterbore in a first face and an attachment member coupled to the plate and comprising a portion inserted in the counterbore of the interbody device.

Yet another embodiment of the invention can include a spinal implant method comprising selecting an attachment member, coupling the attachment member to a plate configured to attach to at least one vertebra and inserting a first portion of the attachment member into a corresponding cavity in an interbody device. The attachment member is rotatable relative to the plate about at least three axes when coupled to the plate such that the interbody device can move relative to the plate. The attachment member and potentially other components can be selected to achieve a desired minimum distance between the interbody device and the plate.

The method can also comprise inserting the interbody device in a space between two vertebrae, rotating the plate relative to the interbody device through the coupling between the plate and the attachment member to position the plate in a desired position and fastening the plate to at least one of the two vertebrae.

According to another embodiment, the method can comprise inserting the interbody device into a space between the two vertebrae and coupling the attachment member to the plate prior to inserting the first portion of the attachment member into the cavity of the interbody device. After the first portion of the attachment member is inserted in the cavity, the method can further include rotating the plate relative to the interbody device through the coupling between the plate and the attachment member to position the plate in a desired position and fastening the plate to at least one of the two vertebrae.

Embodiments of the present invention provide advantages over prior art spinal implant systems and methods by prevent the expulsion of an interbody device.

Embodiments of the present invention can provide an advantage over prior art spinal implant systems and methods by limiting reducing or limiting the impacts between the interbody device and the plate.

Embodiments of the present invention provide another advantage over prior art spinal implant systems and methods by allowing a stabilization plate to be rotated relative to an interbody after the interbody is in place. This allows for better positioning of the plate and reduces or eliminates the need to bend the plate to conform it to the spine.

Embodiments of the present invention provide another advantage by allowing a user to select the depth of insertion of an interbody device relative to a plate. This helps ensure, for example, that the interbody device can be placed near the anterior side of the vertebrae, which is often preferred by surgeons.

BRIEF DESCRIPTION OF THE FIGURES

A more complete understanding of the present invention and the advantages thereof may be acquired by referring to the following description, taken in conjunction with the accompanying drawings in which like reference numbers indicate like features and wherein:

FIG. 12 is a diagrammatic representation of an embodiment of a ring;

FIGS. 13A and 13B are diagrammatic representations of cross-sectional views of various embodiments of rings;

FIGS. 14A and 14B are diagrammatic representations of cross-sectional views of various embodiments of bone screw heads;

FIG. 17 is a diagrammatic representation of an end view of another embodiment of a plate;

FIGS. 18A and 18B are diagrammatic representations of embodiments of channels in a plate.

DETAILED DESCRIPTION OF THE INVENTION

Preferred embodiments of the invention are illustrated in the FIGURES, like numerals being used to refer to like and corresponding parts of the various drawings.

Embodiments of the present invention provide systems and methods for spinal stabilization. In general, a plate attached to one or more vertebrae can prevent expulsion of an interbody device from a disc space. The plate and interbody device can be coupled by an attachment member. According to one embodiment, the attachment member is coupled to the plate and includes a portion inserted in a threaded or non-threaded cavity of the interbody. Preferably, the coupling between the plate and attachment member allows rotation in three dimensions thereby allowing the plate to rotate relative to the interbody. This allows the plate to be better positioned for attachment to the spine during an operation. Additionally, the attachment member and interbody can be shaped so that the interbody is a specified distance away from the plate and consequently a desired distance into the disc space.

Figure 1:
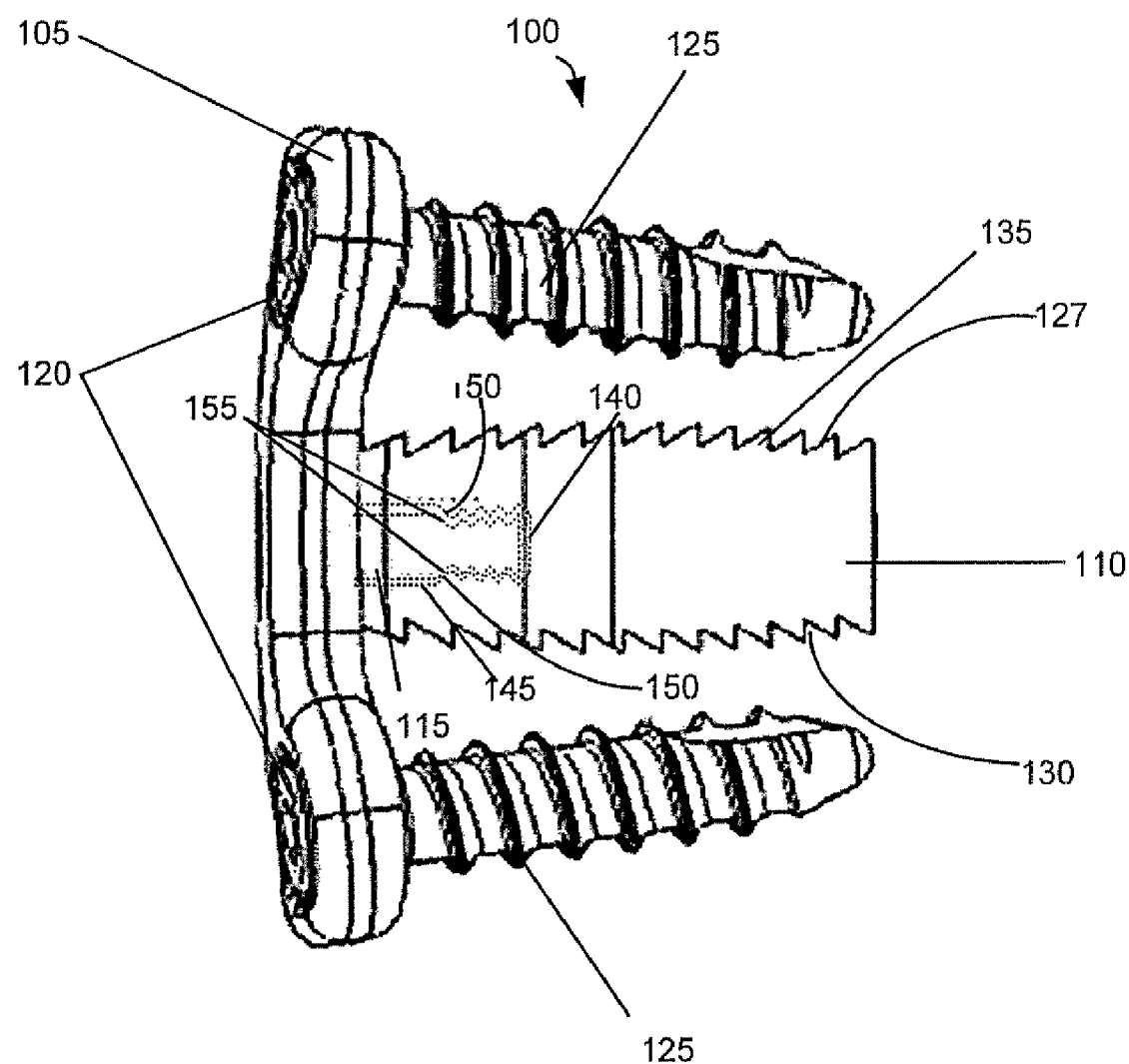
FIG. 1 is a diagrammatic representation of a side view of one embodiment of a spinal implant.

FIG. 1 is a diagrammatic representation of a side view of one embodiment of an implant 100. Implant 100 can include a plate 106 coupled to an interbody device 110 by an attachment member 115. Implant 100 can comprise any biocompatible material, including, but not limited to, titanium, titanium alloy, stainless steel, ceramic material, bone, polymers or combinations thereof. Various portions of implant 100 may be made of different materials and may be radiolucent. For example, interbody device 110 can be formed of PEEK, while plate 105 is formed of titanium. According to another embodiment, both interbody device 110 and plate 105 can both be made of PEEK. In one embodiment, implant 100 is formed of a titanium and aluminum alloy, such as Ti6Al4V-Eli.

Plate 105 can be flat, curved, or have any suitable form factor for spinal surgery. Generally, plate 105 includes holes 120 for fasteners 125 that allow plate 105 to be attached to the appropriate vertebrae. Examples of fasteners include, but are not limited to, bone screws, nails, rivets, trocars, pins, barbs or other threaded or non-threaded member which is securable within or to bone. According to one embodiment, bone screws can be attached to plate 105 in a manner that allows for polyaxial rotation prior to attachment to the bone. One example of a mechanism for attaching a plate to vertebrae that allows for polyaxial rotation of bone screws is described in U.S. patent application Ser. No. 10/036,012, entitled "System and Method for Stabilizing the Human Spine with a Bone Plate," by Wagner et al., filed Dec. 26, 2001, which is hereby fully incorporated by reference herein. Plate 105 may be attached to the spine with any number of fasteners.

Interbody device 110 may have a variety of different form factors and sizes. For example, face 127 may be angled relative to face 130 so that a desired angle of lordosis is achieved when implant 100 is in place. In other words, the outer faces of interbody device 110 may be sloped to allow an anterior side height to differ from a posterior side height. In addition to a slope, faces 127 and 130 may be curved. This curvature may allow outer faces 127 and 130 to substantially conform to the shapes of vertebral surfaces, particularly the anatomical domes of the respective vertebra.

Various surfaces of interbody device 110 can be treated to promote osseointegration. For example, outer faces 127 and 130 can be coated with titanium plasma spray, bone morphogenic proteins, hydroxyapatite and/or other coatings. In addition to or instead of coating outer faces 127 and 130, outer faces 127 and 130 may be roughed by processes such as, but not limited to, chemical etching, surface abrading, shot peening, electric discharge roughening or embedding particles in the surface.

Interbody device 110 may include a number of protrusions 135 that can extend into adjacent vertebrae to better hold interbody device 110. Protrusions 135 can be arranged in rows of teeth, in radial rows or other arrangements with any number of protrusions. Protrusions 135 can extend any distance, but preferably are at least 0.2 mm to 1 mm long. According to one embodiment, protrusions 135 may be arranged as rows of teeth configured to "bite" into the vertebrae as interbody device 110 is implanted. In the example shown, the teeth are angled to prevent interbody device 110 from shifting to the right, thereby reducing movement away from plate 105.

According to one embodiment, interbody device 110 can include a cavity 140 to receive attachment member 115. Cavity 140 and attachment member 115 can be configured so that interbody device 110 is a desired minimum distance from plate 105. This allows the depth of insertion of interbody device 110 into the space between the vertebrae to be controlled (i.e., a greater distance between interbody device 110 and plate 105 will lead to a greater depth of insertion).

Because of the angle of forces in the spine, interbody device 110 will tend to be pressed towards plate 105 during use (i.e., towards the left side of the page in FIG. 1). Consequently, cavity 140 can be a counterbore into which attachment member 115 inserts without further attachment. In this case cavity 140 and the portion of attachment member inserted in cavity 140 can be unthreaded. If additional attachment is desired to prevent interbody device 110 from detaching from attachment member 115, cavity 140 and attachment member 115 can be threaded as shown in FIG. 1. According to one embodiment, cavity 140 can include a threaded portion and a countersunk portion 145. Surface 150 can abut shoulder 155 to limit the depth of insertion of attachment member 115. The depth of countersunk portion 145 and the distance between plate 105 and shoulder 155 can be configured to limit the closeness of interbody device 110 and plate 105 and thereby control the minimum insertion distance of interbody 110 into the disc space.

Figure 2A:
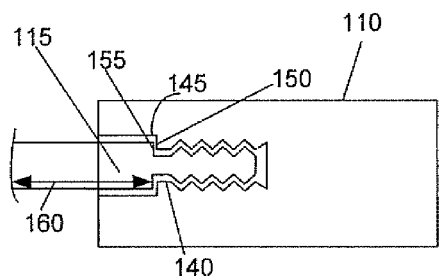
FIGS. 2A-2D are diagrammatic representations of various embodiments of shaping an interbody and attachment member.

Attachment member 115 and cavity 140 can be otherwise shaped to control the distance between interbody device 110 and plate 105. Turning briefly to FIGS. 2A-2D, various embodiments of attachment member 115 inserted in cavity 140 are shown. In FIG. 2A, interbody device 110 includes a countersunk portion 145. Attachment member can include a straight shoulder 155 that abuts the surface 150 of countersunk portion 145. In other embodiments shoulder 155 can be beveled, curved or otherwise shaped. Based on the depth of the countersink, and length 160 from plate 105 to shoulder 155, the closeness of interbody device 110 to plate 105 can be controlled.

Figure 2B:
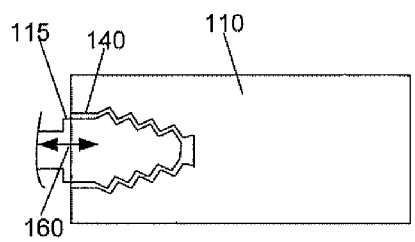

In FIG. 2B, attachment member 115 includes a tapered threaded portion and interbody device 110 a corresponding tapered cavity 140. The taper of attachment member 115 and cavity 140 can determine how far attachment member 115 can be threaded into interbody device 110. This, combined with length 160 to the tapered threading, limits how close interbody device 110 is to plate 105.

Figure 2C:
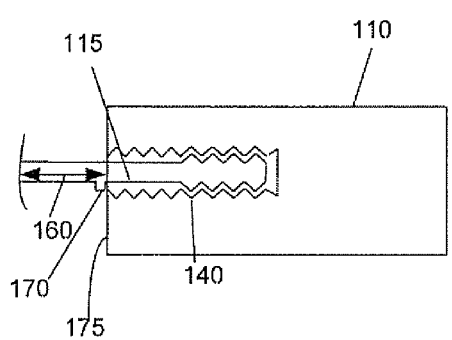

In the embodiment of FIG. 2C, attachment member 115 can include protrusion 170 that abuts the outer surface 175 of interbody device 110 (or a counterbore surface or other surface) to limit how far attachment member 115 can be threaded into interbody device 110. In this case, the length 160 from plate 105 to the surface of protrusion 170 that abuts interbody device 110 determines the distance between plate 105 and interbody device 110.

Figure 2D:
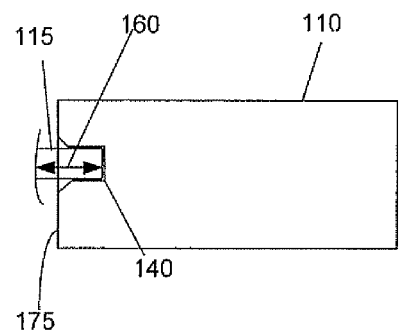

In FIG. 2D, cavity 140 is simply a counterbore with unthreaded sides. Attachment member 115 also has unthreaded surfaces and simply abuts a surface of cavity 140. The closeness of interbody device 110 to plate 105 is limited by the length 160 of attachment member 115 and the depth of cavity 140. Thus, attachment member 115 and interbody device 110 can be shaped so that interbody device 110 is a selected distance from plate 105.

Surgical kits for implant 100 can include any number of plates 105, attachment members 115 and interbody devices 110. For example, a surgical kit for implant 100 can include a number of small, medium and large interbody devices 110 that can vary in length, width, height or other dimension. Additionally, interbody devices 110 with various slopes can be provided. This allows the surgeon to form implant 100 to have the appropriate sized interbody device 110 for a patient and to achieve desired lordotic adjustment. The interbodies and attachment members can be color coded and/or include other indicia to indicate size, slope, offsets and other parameters.

Moreover, various interbody devices 110 and attachment members 115 can be provided to allow a surgeon to select the depth of insertion of a selected interbody device 110 relative to plate 105. For example, a surgical kit can contain an interbody device 110 with a set countersink and a variety of attachment members 115 that have different offsets to a stop or shoulder. By selection of the appropriate attachment member, the surgeon can select how far into the disc space interbody device 110 is implanted. Alternatively, a single attachment member and various interbody devices 110 can be provided. The various interbody devices 110, for example, can have countersinks of various depths to achieve a desired distance between a selected interbody device 110 and plate 105. Additionally, the cavities to receive the attachment members can be located differently on different interbodies. This allows the surgeon to select whether the interbody device will be inserted at a particular angle to the spine (e.g., from an anterior or lateral approach). In other embodiments, multiple interbodies and attachment member can be provided.

Figure 3:
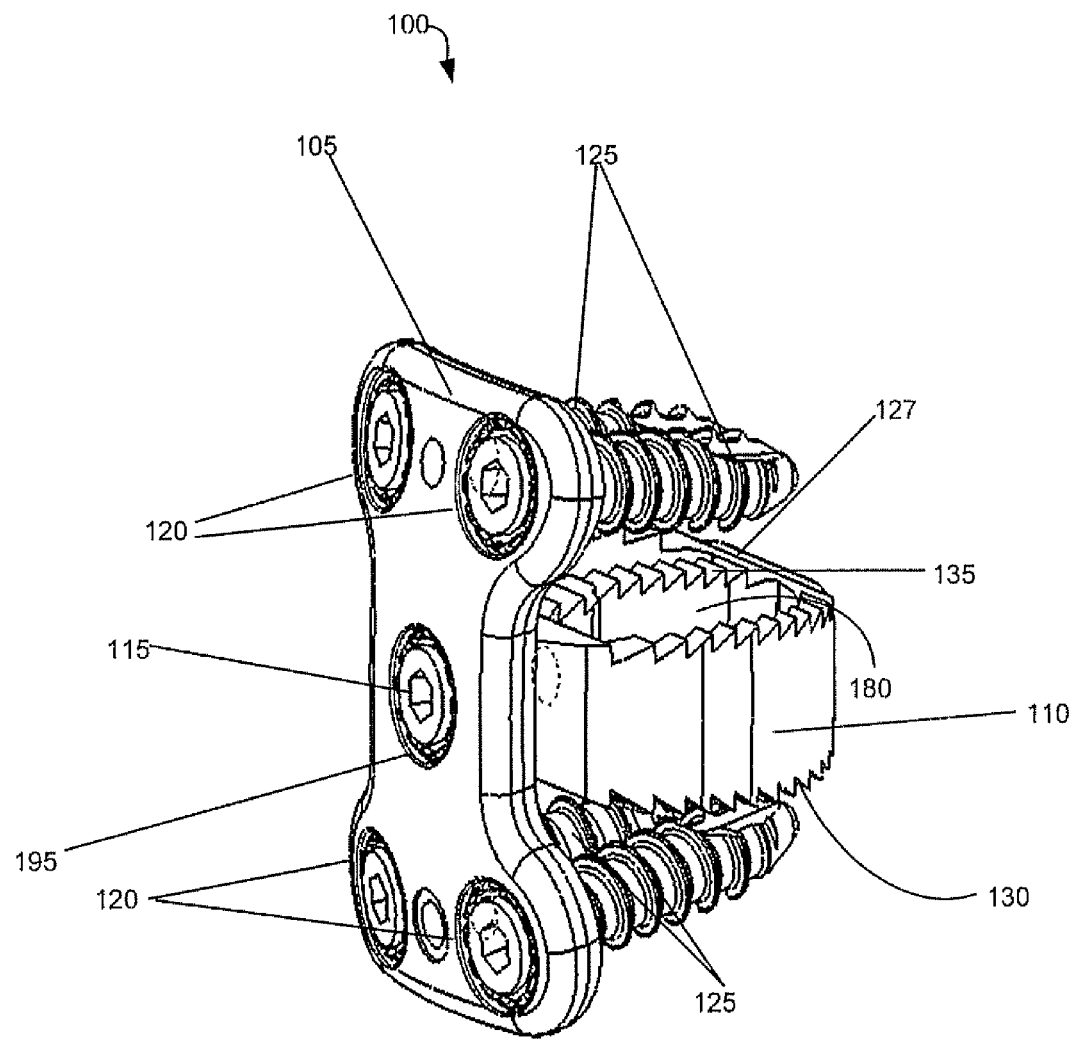
FIG. 3 is a diagrammatic representation of an oblique view of one embodiment of a spinal implant.

FIG. 3 is a diagrammatic representation illustrating an oblique view of one embodiment of implant 100, emphasizing surface 127 of interbody device 110 and showing features such as protrusions 135, discussed above. While shown as having a generally oblong shape, interbody device 110 can have a rectangular, square, circular or other shape. FIG. 3 further illustrates that interbody device 110 can include channels, such as channel 180, running from surface 127 to surface 130. While shown as having a substantial area compared to the overall area of interbody device 110 the channels 180 can be relatively small and more numerous, not present at all or otherwise configured. The channels 180 can allow bone to pass as bone growth occurs, thereby allowing the vertebrae to fuse together. Additionally, the 180 channels can be packed with bone growth material. By way of example, but not limitation, the bone growth material can include autograft bone (such as bone from the patient's lilac crest), allograft bone, synthetic bone growth material or combinations thereof. FIG. 3 further illustrates holes 120 for fasteners to attach plate 105 to the adjacent vertebrae and hole 195 for attachment member 115. As will be discussed in more detail below, attachment member 115 and fasteners 125 can be coupled to plate 105 in a manner that allows attachment member 115 and fasteners 125 to rotate in multiple directions relative to plate 105.

Figure 4:
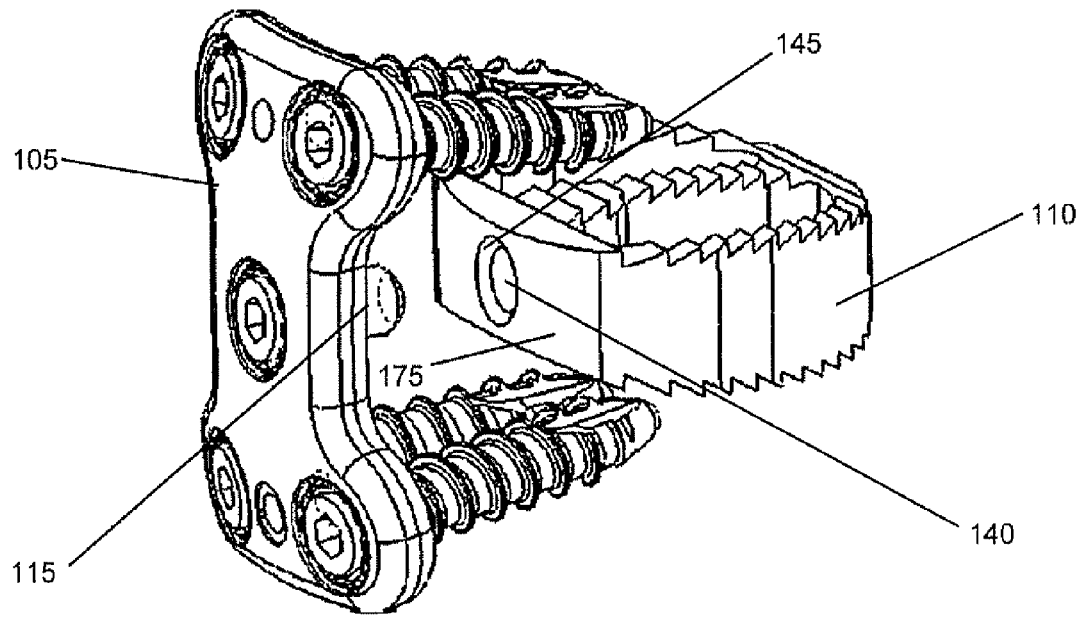
FIG. 4 is a diagrammatic representation of a partially exploded view of one embodiment of a spinal implant.

FIG. 4 is a diagrammatic representation of a partially exploded view of one embodiment of implant 100 including plate 105, interbody device 110 and attachment member 115. In particular, FIG. 4 emphasizes surface 175 of interbody device 110 having an opening to cavity 140. Cavity 140, as shown in FIG. 4, can be a counterbore. A portion of attachment member 115 can be inserted in the counterbore and abut the surface of countersunk portion 145 to limit how far attachment member 115 is inserted into interbody device 110. In the example of FIG. 4, both cavity 140 and the corresponding portion of attachment member 115 are unthreaded.

As described in the above embodiments, interbody device 110 can be attached to plate 105 in a manner that limits the closeness of plate 105 to interbody device 110. According to one embodiment, interbody device 110 and attachment member 115 can be shaped to achieve a gap having a particular minimum size between interbody device 110 and plate 105. Preferably, interbody device 110 includes a female threaded cavity with a countersunk portion. Attachment member 115 can include a threaded portion and a shoulder that abuts the surface of the countersink. Attachment member 115 can be in a fixed position relative to plate 105, integrated with plate 105 or otherwise coupled to plate 105. In other embodiments, however, attachment member 115 can be attached to plate 105 in a manner that allows movement between attachment member 115 and plate 105. Preferably, attachment member 115 is attached in a manner that allows plate 105 to rotate in three directions relative to interbody device 110 prior to attaching plate 105 to the vertebrae. Various, non-limiting examples of allowing movement of plate 105 relative to interbody device 110 are discussed below in conjunction with FIGS. 5-18.

Figure 5:
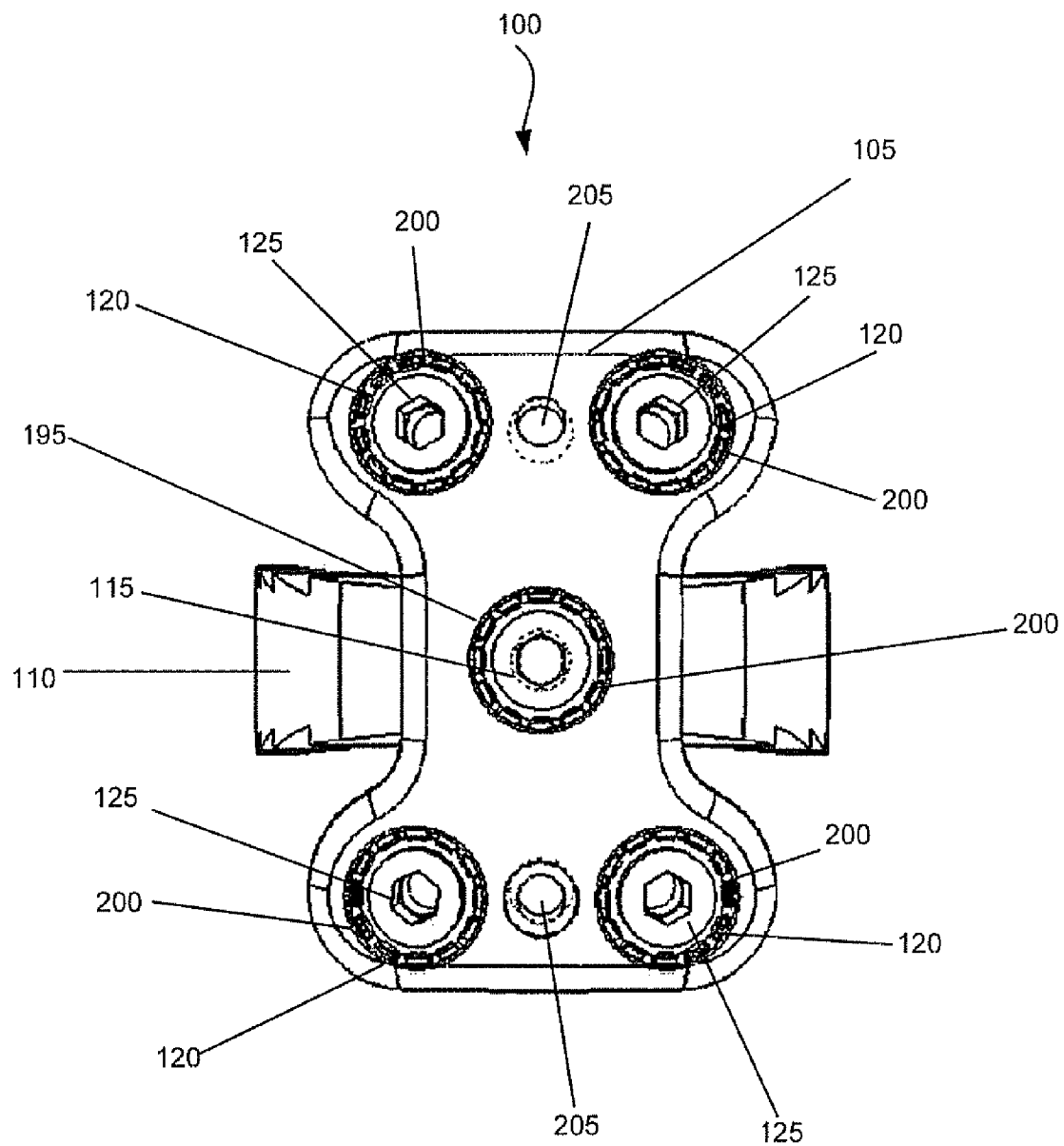
FIG. 5 is a diagrammatic representation of an end view of one embodiment of a spinal implant.

FIG. 5 is a diagrammatic representation of an end view of one embodiment of implant 100, including plate 105, interbody device 110 and attachment member 115. For an anterior procedure, FIG. 5 represents an anterior view. Plate 105 includes fastener holes 120 shaped to receive the heads of fasteners 125 and attachment member hole 195 to receive a head of attachment member 115. For ease of manufacturability, holes 120 and 195 can be the same size and the head of attachment member 115 can be similar to the heads of fasteners 125. Rings 200 can be disposed in holes 120 and 195. While all rings 200 are shown as being identical in FIG. 5, the rings may have different dimensions. Preferably, rings 200 include a gap, or other feature that allows rings 200 to contract under pressure. In general, rings 200 allow fasteners 125 and attachment member 115 to be rotated to a variety of orientations relative to plate 105, as discussed below in conjunction with FIGS. 6-16. Plate 105 can also include holes 205 that can strengthen plate 105 under compressive loads.

In the example of FIG. 5, only one attachment member hole 195 is shown. However, other embodiments may include multiple attachment member holes 195 at different locations to allow a surgeon to select various positions of interbody device 110 relative to plate 105. Furthermore, while four fastener holes 120 are shown, other embodiments may include more or less fasteners.

Figure 6:
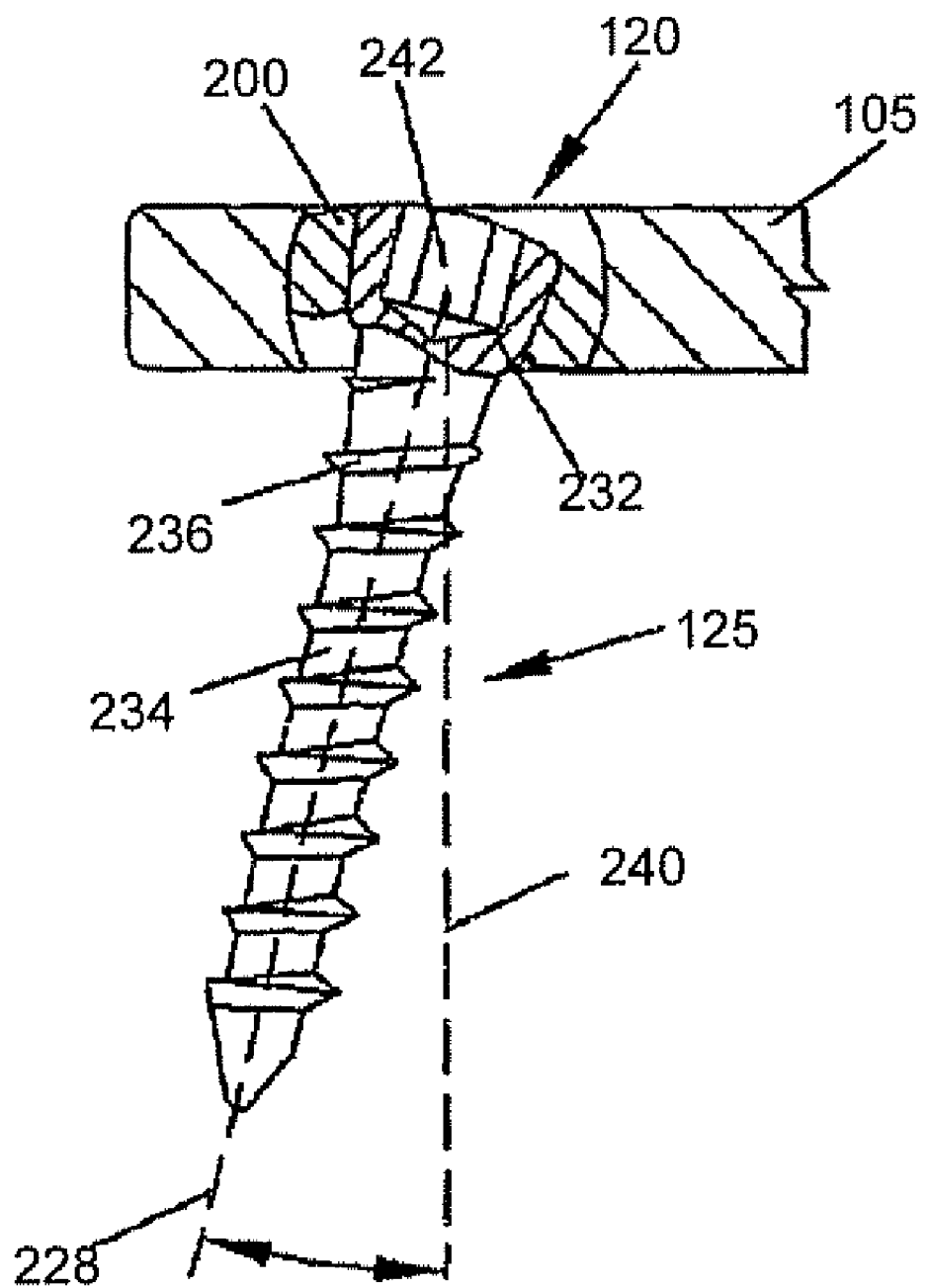
FIG. 6 is a diagrammatic representation of one embodiment of a bone screw attached to a plate.
Figure 7:
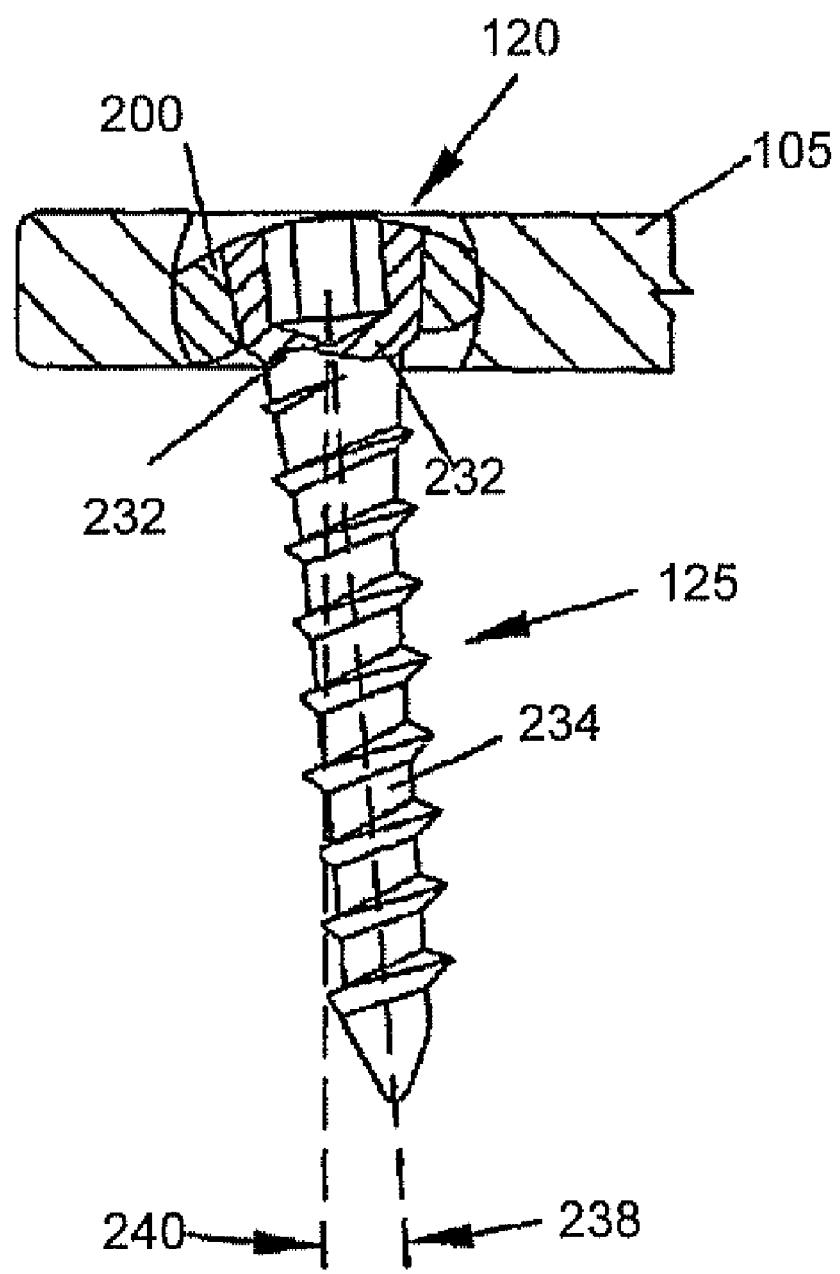
FIG. 7 is a diagrammatic representation of another embodiment of a bone screw attached to a plate.

FIG. 6 depicts a cross-sectional view of an embodiment of one of the holes 120 (also shown in FIG. 5) in which screw 125 is disposed. Hole 120 is preferably substantially spherical in shape so that a head 232 of screw 125 may be rotated and moved to various positions within hole 120. Ring 200 is preferably sized to fit into hole 120 between plate 105 and head 232. The outer surface of ring 200 is preferably curved to permit movement of the ring within hole 120. The combination of ring 200 and hole 120 is like that of a ball and socket since ring 200 may be rotated both horizontally and vertically in clockwise and counterclockwise directions within hole 120. Ring 200 may also be rotated in directions that are angled away from the horizontal and vertical directions. In FIG. 6, ring 200 at least partially surrounds head 232 of screw 125 which is positioned within hole 120. A shank 234 of bone screw 125 preferably has threading 236 to allow the screw to be inserted into a bone when it is rotated in a clockwise direction. Head 232 preferably includes a cavity 242 that extends from the top of the head to an inner portion of the head. Cavity 242 may be shaped to receive the end of any fastening device e.g., a socket wrench that may be used to turn screw 125.

Screw 125 may be simultaneously screwed into a bone and moved to its desired position. The inner surface of ring 200 and the outer surface of head 232 are preferably tapered and shaped to mate with each other. The bottom portion of head 232 is preferably smaller than the upper portion of ring 200. As screw 125 is inserted into a bone, head 232 preferably applies a radial force to ring 200, thereby causing the ring to expand within the hole and increase the size of the ring's gap. An interference fit may form between screw head 232, ring 200, and plate 105 in which these elements fit so tightly together that they obstruct the movements of each other. The hoop stress of ring 200 on head 232 may fixedly attach screw 125 to plate 105. Also during insertion of screw 125, screw head 232 and ring 200 may be positioned within hole 120 such that their left sides are at a higher elevation than their right sides. FIG. 6 shows that positioning screw head 232 in this configuration may result in a centerline 228 of shank 234 being obliquely angulated with respect to plate 105. In fact, centerline 238 may be positioned where it is at an angle ranging from 0 to 15 degrees with respect to an imaginary axis 240 which is perpendicular to plate 105 FIG. 6 demonstrates shank 234 of screw 125 being angled to the left of imaginary axis 240 while FIG. 7 demonstrates shank 234 being angled to the right of imaginary axis 240. Screw 125 is not limited to these positions and can be angled in various directions, such as into the page.

Figure 8:
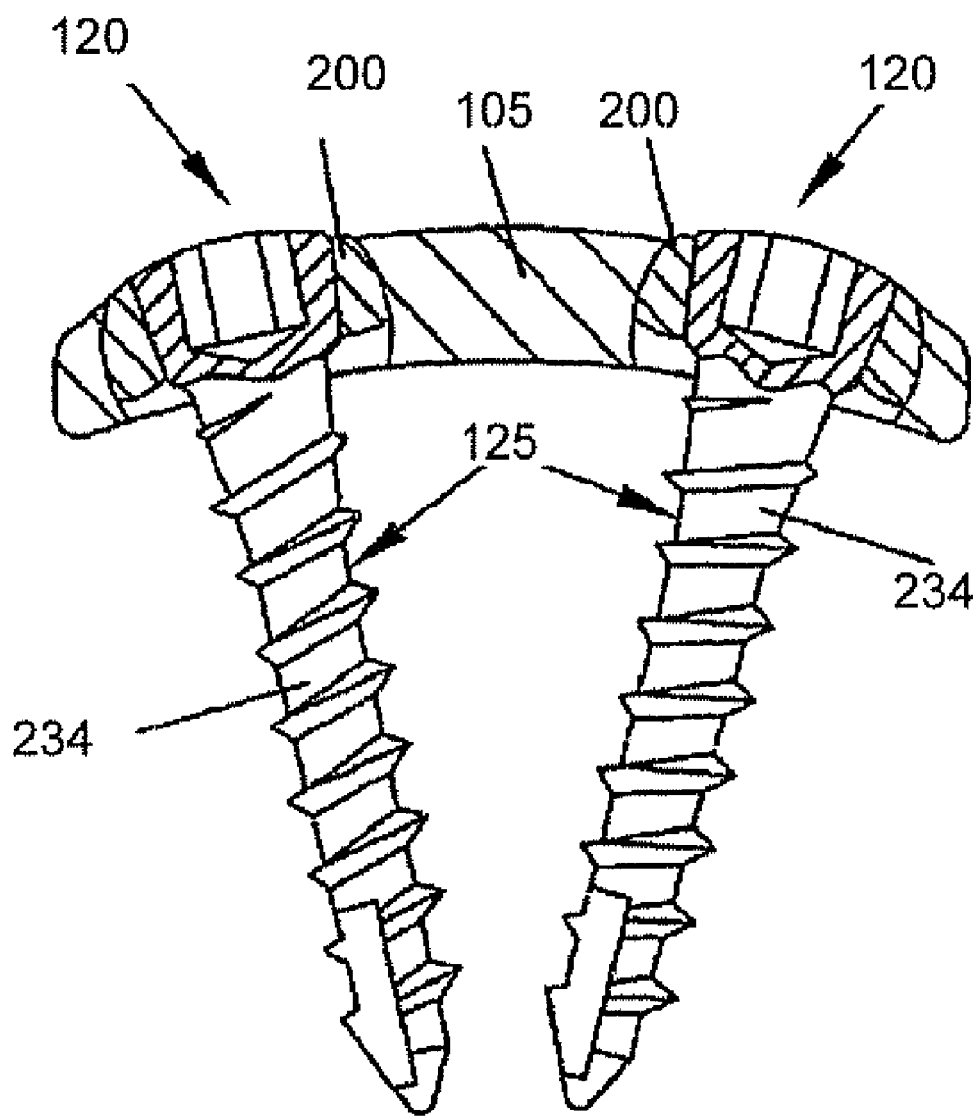
FIG. 8 is a diagrammatic representation of an embodiment of multiple bone screws attached to a plate.
Figure 9:
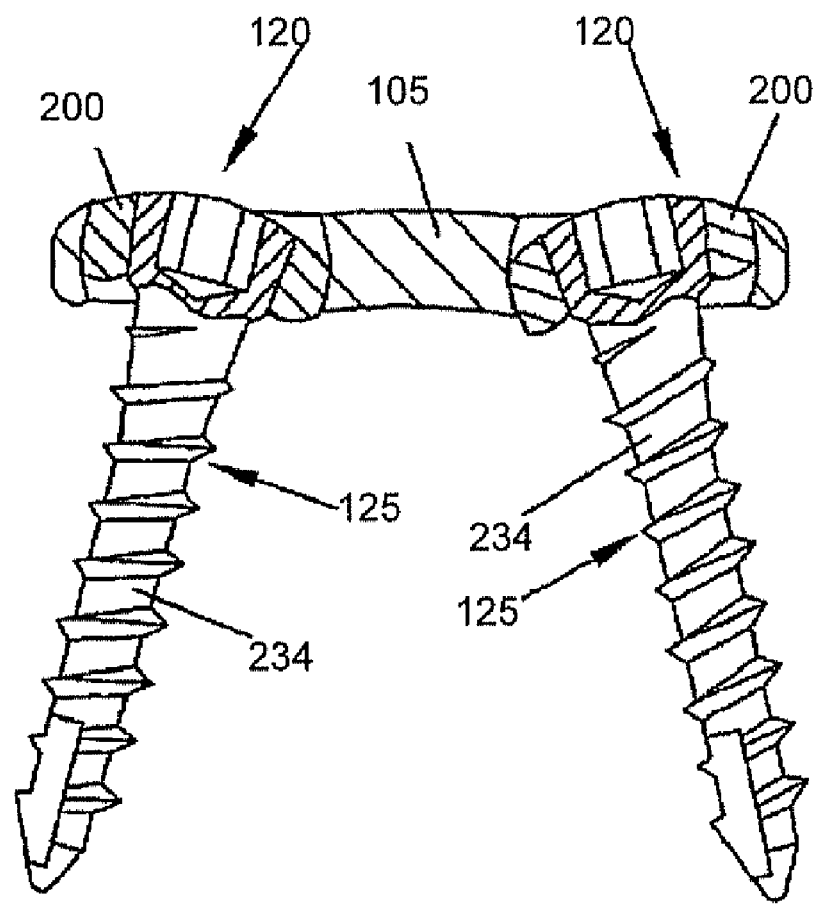
FIG. 9 is a diagrammatic representation of another embodiment of multiple bone screws attached to a plate.

FIGS. 8 and 9 depict different embodiments of end plate 105 with fasteners inserted FIG. 8 shows that screws 125 may be positioned within holes 120 such that they extend in converging directions with respect to each other. The screws 125 depicted in FIG. 9, on the other hand, are shown as being positioned such that their shanks 234 extend in diverging directions with respect to each other. Screws 125 may be moved to such positions as described above. Since bone screws 125 may be placed in diverging or converging directions through holes 120 at both ends of plate 105, screw backout may be greatly reduced. Further, the use of rings 200 to fixedly attach screws 125 to plate 105 may prevent damage to tissue structures by any screws that are able to escape from the bone. Rings 200 preferably do not extend above the upper surface of plate 105, and thus advantageously do not contact tissue structures. Screw 125 may be placed in a uni-cortical position within the bone since the problem of screw backout is greatly reduced by the diverging or converging screw configurations.

Figure 10:
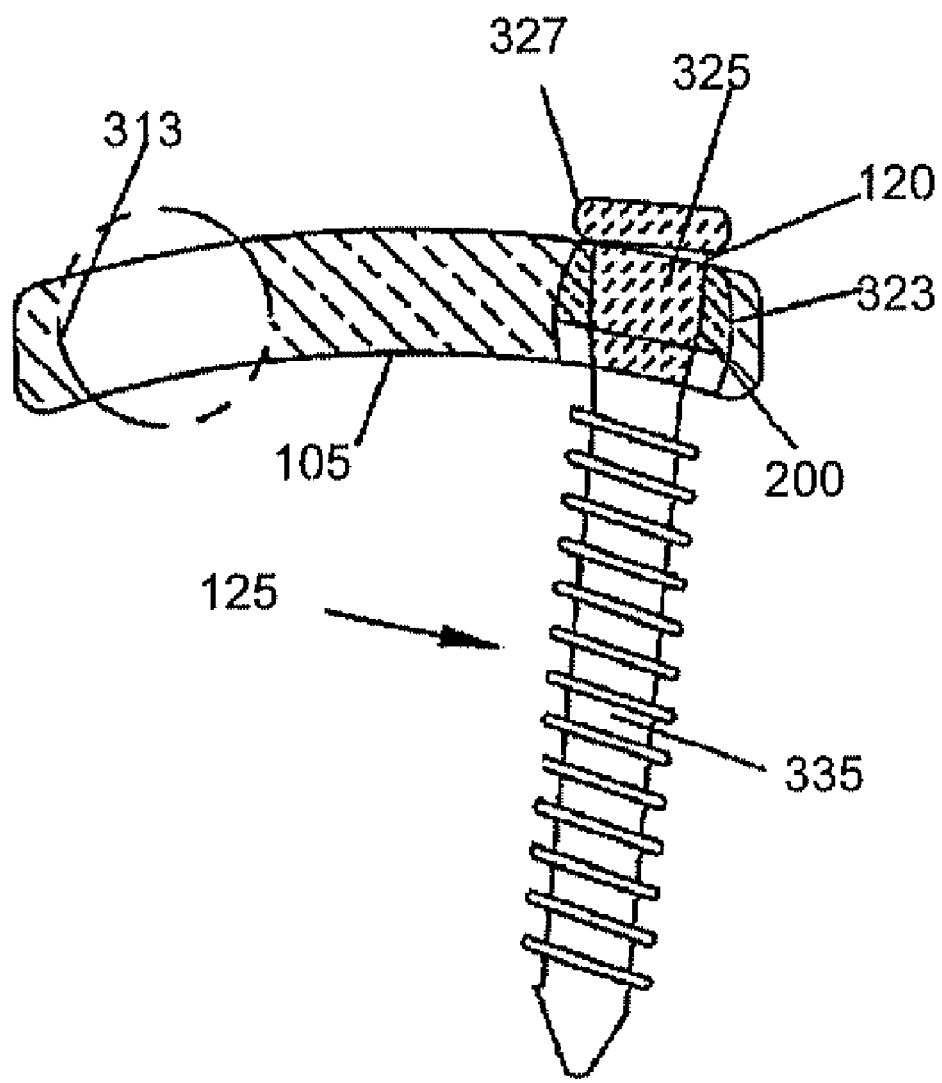
FIG. 10 is a diagrammatic representation of another embodiment of a bone screw and plate.

A side view of another embodiment of a spinal plate 105 and fasteners is shown in FIG. 10. This embodiment includes a bone screw 125 and a ring 200. Plate 105 may be used to stabilize a bony structure such as the spine to facilitate a bone fusion (e.g., a spinal fusion). The bone screw 125 may be used to connect plate 105 to a bone such as a vertebra. Ring 200 preferably fixes bone screw 125 to plate 105 at a selected angle that depends upon the patients anatomy.

In this embodiment, each hole 120 preferably has a curvate inner surface 313 for engaging the outer surface 323 of ring 200. The inner surface 313 preferably has the shape of a portion of an outer surface of a sphere. Hole 120 has a width that is defined across the inner surface 313 of the borehole. The width of the borehole may vary in a direction axially through the borehole. For example, the width of the holes preferably increases from a surface of the plate 105 to about the middle of the plate 105. The width of the hole 120 preferably decreases from about the middle of the plate 105 to an opposite surface of the plate 105 such that the hole has a maximum width near the midpoint between the surfaces.

The outer surface 323 of ring 200 is preferably curvate for engaging the inner surface 313 of the borehole. The shape of surfaces 323 and 313 preferably allow ring 200 to swivel within the borehole. The swiveling action may be similar to that of a ball and socket joint. The ring 200 preferably surrounds at least a portion of the head 325 of a bone screw 125. The enlarged end 327 disposed on head 325 is optional and need not be included if it inhibits angulation of the bone screw 125. The swiveling of the ring 200 within the borehole preferably enables the shank 335 of the bone screw 320 to rotate in a substantially conical range of motion. In this manner, the head 325 is preferably movable within the borehole, and the shank 335 is adjustably positionable at a plurality of angles substantially oblique to the plate 105.

In an embodiment, the surfaces 323 and 313 are preferably shaped to provide a conical range of motion to the shank 335 that is within a preferred range of angles. The head 325 is preferably movable within the borehole such that the shank 335 can be positioned at a selected angle relative to an imaginary axis running perpendicular to the plate 105 proximate borehole 120. The selected angle is preferably less than about 45 degrees, more preferably less than about 30 degrees, and more preferably still less than about 15 degrees.

Ring 200 preferably has an outer width that is less than or about equal to the width of hole 120 at a location between the surfaces of plate 105. In this manner, ring 200 may be positioned within hole 120 proximate the middle of the hole to enable the bone screw 125 to extend substantially perpendicularly from the bone plate 105. Prior to surgery, rings 200 are preferably pre-positioned within holes 120 of plate 105. "Pre-positioned" is taken to mean that the rings are capable of swiveling within the borehole but are preferably inhibited from falling out of the borehole because of the reduced width of the borehole proximate the upper and lower surfaces. The width of the borehole proximate the upper and lower surfaces of plate 105 is preferably less than or about equal to the outer width of the ring 200 to inhibit the ring from failing out of the borehole. In this manner, the surgeon may use a plate 105 having rings 200 pre-positioned within the holes 120 such that the rings 200 will not fall into the surgical wound when implant 100 is installed. Alternately, the rings 200 can be manually positioned within holes 120 during surgery.

Ring 200 preferably includes one or more slots or gaps. The slot preferably allows the ring 200 to be contracted or expanded. Contraction of ring 200 may allow the ring 200 to be positioned within the borehole during surgery. Once positioned within the borehole the ring 200 preferably expands and is inhibited from falling out of the borehole.

Ring 200 is preferably capable of being swiveled such that one portion of the ring 200 is adjacent to one surface of plate 105 while another portion of the ring 200 lies adjacent to the opposite surface of plate 105. Ring 200 is preferably sufficiently thin to allow it to reside within the borehole without extending from the borehole beyond the surfaces of plate 105. Generally, it is preferred that the ring 200 and screw head 325 remain within the hole 120 to minimize the profile of implant 100. In some embodiments, however, the bone screw 125 may be capable of being angulated relative to the plate 105 such that ring 200 extends from the hole 120 beyond a surface of the plate 105.

The head 325 is preferably screwed into ring 200 to create a fixed connection between bone screw 125 and plate 105 at a selected angle. In an embodiment depicted in FIG. 11, screw head 325 preferably contains head threading 321 on its outer surface that is complementary to ring threading 319 contained on the inner surface of ring 200. The head threading 321 preferably mates with the ring threading 319 to enhance the connection between the bone screw 125 and the ring 200. The head 325 preferably has a cavity 342 formed on its upper surface for receiving a driving tool such as a screw driver or an alien wrench.

It is believed that using a threading engagement between the head 325 and ring 200 increases the hoop stress exerted on head 325, resulting in a stronger connection between the bone screw 125 and the plate 105. Moreover, if bone threading 336 becomes loose within a bone, screw backout from plate 105 will tend to be resisted by the threaded connection between the screw head 325 and the ring 200. Thus, even if the shank 335 loosens within the bone, the head will tend to remain within the borehole of the plate so as not to protrude from the plate into surrounding body tissue.

Figure 11:
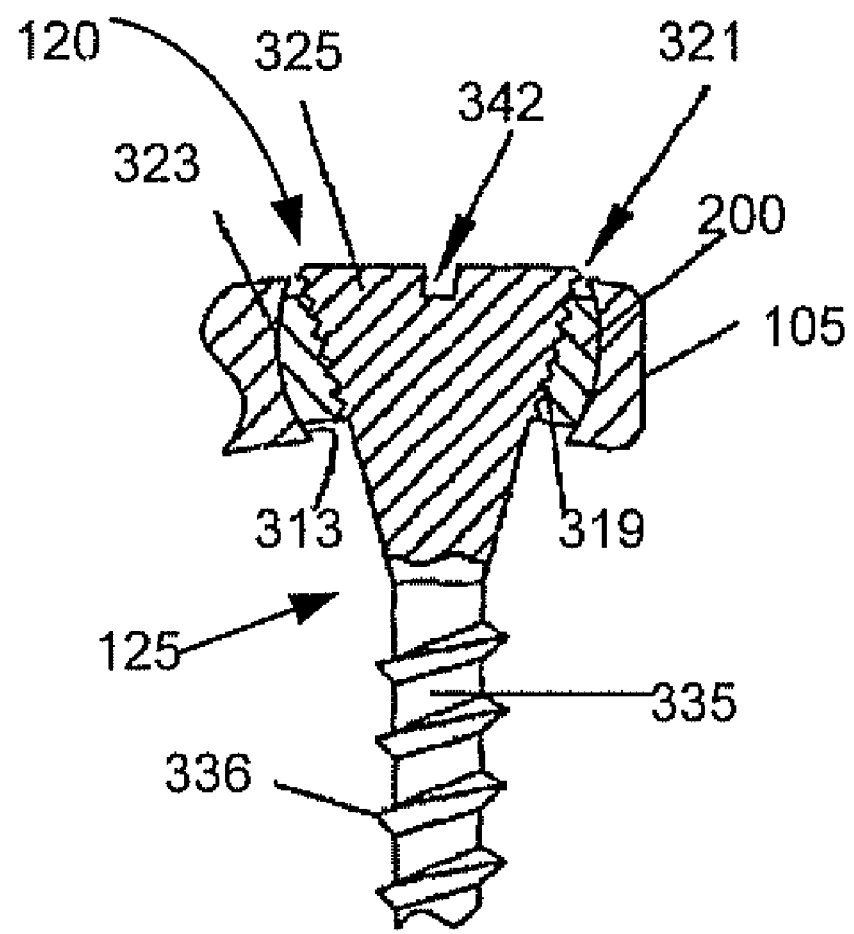
FIG. 11 is a diagrammatic representation of yet another embodiment of a bone screw and plate.

As shown in FIG. 11, the head threading 321 on the head 325 and the ring threading 319 on the inner surface of ring 200 is preferably substantially fine relative to the threading 336 on bone screw 125. That is, the pitch of the head threading 321 and ring threading 319 is preferably smaller than that on bone screw 125. The ring threading 319 preferably has multiple starts to facilitate connection of the bone screw and the ring. In one embodiment, the ring threading 319 has a double start such that the head can be started into the ring threading at either one of two orientations offset by 180 degrees. In another embodiment, the ring threading has a triple start such that the head can be started into the ring threading at any one of three orientations offset by 420 degrees.

The ring threading 319 and head threading 321 are preferably pitched to a substantially similar degree to the threading 336 on the bone screw 320. Preferably, the ring threading 319 and head threading 321 are pitched such that the head 325 causes expansion of the ring 200 while the bone screw 320 is being inserted into the bone.

During the surgical procedure for attaching the plate 105 to a bone, holes may be drilled and tapped into the bones to which plate 105 is to be attached. Plate 105 may then be positioned adjacent to the bones. A ring 200 may be positioned within the borehole. A bone screw 125 may be positioned through ring 200 such that the head threading 321 of head 325 engages the ring threading 319 of ring 200. The bone screw 125 may then be rotated to insert the bone screw into the bone. As the screw is rotated the head threads and ring threads preferably interact such that the head is moved into the ring. Movement of the head 325 into the ring 200 preferably causes the ring to expand such that the orientation of the bone screw 320 relative to the plate 105 is fixed. Preferably, the ring threading and head threading is pitched such that the orientation of the bone screw 125 is fixed after plate 105 engages the bone.

The bone screws may be used in pairs to prevent screw backout. The bone screws are preferably positioned into the bone in substantially converging or substantially diverging directions relative to one another.

The outer surface of the head 325 is preferably tapered so that screwing the head into the ring causes a change in width (e.g., expansion) of the ring 200 to fix the bone screw 320 in position relative to the plate 105. The inner surface of the ring 200 may also be tapered to substantially match the taper on the outer surface of the head. At least a portion of the head 325 preferably has a width greater than the inner width of the ring 200. As the screw head is screwed into the ring 200, the ring preferably expands outwardly from its inner surface to accommodate the increasing width of the screw head 325. The ring 200 may contain a slot or gap as previously described to facilitate expansion of the ring against the inner surface 313 of the hole 120. The slot is preferably widened as a result of force received from head 325. The force exerted by head 325 against the inner surface of ring 200 preferably presses the ring into a fixed engagement against inner surface 313 of hole 120.

Alternatively, ring 200 may contain one or more partial slots 345, as depicted in FIG. 12. Each partial slot 345 preferably extends from a top 347 or bottom 349 of ring 200 into the ring. Partial slots may extend up to about midpoint 348 of ring 200. In one embodiment, a plurality of slots 345 may be oriented about the ring such that alternate slots extend from the top 347 and/or the bottom 349 of ring 200, as depicted in FIG. 12. These alternating partial slots preferably facilitate the expansion and contraction of ring 200.

Cross-sectional views of two embodiments of ring 200 having threaded section 319 are shown in FIGS. 13A and 13B. The ring may contain an inner surface that is tapered (as shown in FIG. 13A) or that is substantially non-tapered (as shown in FIG. 13B). Cross sectional views of two embodiments of screw 125 are shown in FIGS. 14A and 14B. The head 325 may have a substantially non-tapered outer surface 331 (as shown in FIG. 14A) or a substantially tapered outer surface 331 (as shown in FIG. 14B). It is to be understood that each of the heads of the screws depicted in FIGS. 14A and 14B may be used in combination with either of the rings 200 depicted in FIGS. 13A and 13B. It is also to be appreciated that the head of the screw may include an outer surface having a substantially non-tapered portion along with a tapered portion proximate its end for expanding the ring 200.

As described herein, a "ring" is taken to mean any member capable of fitting between the inner surface 313 of a fastener hole and the bone screw 125 to connect the bone screw to the plate 105. The ring is preferably substantially circular to surround head 325, but the ring may instead have a non-circular shape. The ring may be made of a number of biocompatible materials including metals, plastics, and composites.

Figure 15:
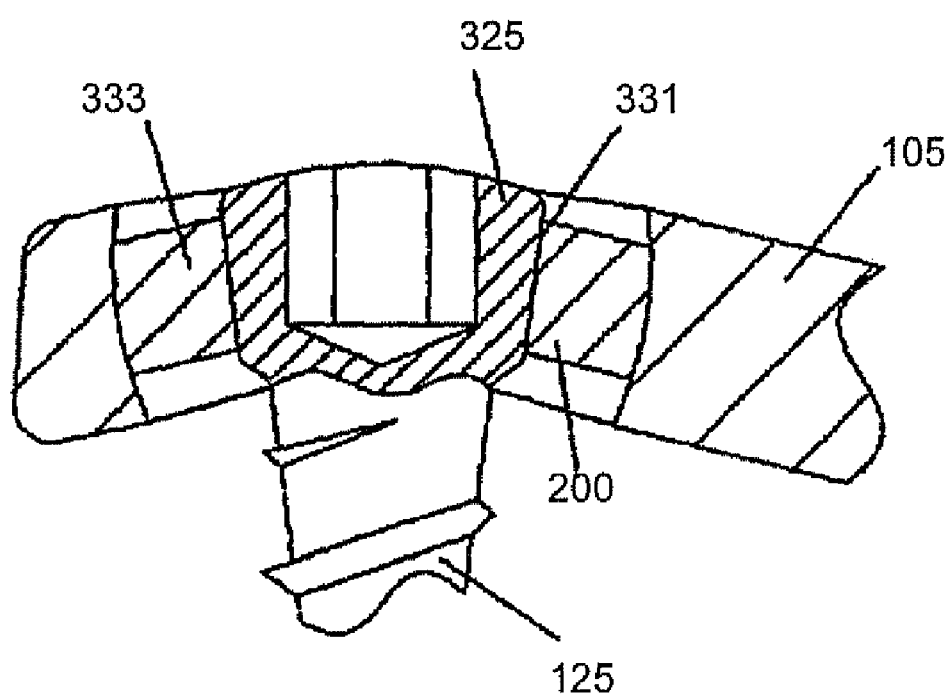
FIG. 15 is a diagrammatic representation of another embodiment of a bone screw and end plate.

In an embodiment, a stronger connection between the bone screw 125 and the plate 105 may be formed by texturing either outer surface 331 of head 325 of bone screw 125 or inner surface 333 of ring 200, as depicted in FIG. 15. Preferably, both surfaces are textured to inhibit movement of the bone screw with respect to the plate. During typical manufacturing procedures, outer surface 331 of head 325 and inner surface 333 of ring 200 may be formed as relatively smooth surfaces.

While the friction between these smooth surfaces tends to be sufficient to maintain bone screw 125 in a fixed position with respect to plate 105, under stressful conditions the bone screw may be forced out of ring 200. By providing at least one textured surface, the coefficient of friction of the surface may be increased so that a large amount of force is needed to overcome the frictional connection between head 325 of bone screw 125 and ring 200. This increase in friction between bone screw 125 and ring 200 may further inhibit screw backout from plate 105.

A number of textured surfaces may be used to increase the coefficient of friction between ring 200 and head 325 of bone screw 125. In general, any process which transforms a relatively smooth surface into a roughened surface having an increased coefficient of friction may be used. Methods for forming a roughened surface include, but are not limited to: sanding, forming grooves within a surface, ball peening processes, electric discharge processes, and embedding of hard particles within a surface.

In one embodiment a plurality of grooves may be formed in outer surface 331 of head 325 of bone screw 125 or inner surface 333 of ring 200. Preferably, a plurality of grooves is formed in both outer surface 331 and inner surface 333. While it is preferred that both outer surface 331 and the inner surface 333 be textured, texturing of only one of the surfaces may be sufficient to attain additional resistance to movement.

In another embodiment, the frictional surface may be created by an electrical discharge process. An electrical discharge process is based on the principle of removal of portions of a metal surface by spark discharges. Typically a spark is generated between the surface to be treated and an electrode by creating potential differential between the tool and the electrode. The spark produced tends to remove a portion of the surface disposed between the electrode and the surface. Typically, the electrode is relatively small such that only small portions of the surface are removed. By moving the electrode about the surface numerous cavities may be formed within the surface. Typically these cavities are somewhat pyramidal in shape. Various patterns may be formed within the surface depending on how the electrode is positioned during the discharge. Electric discharge machines are well known in the art. A method for forming a frictional surface within a metal surface using an electric discharge process is described in U.S. Pat. No. 4,964,641 to Miesch et al. which is incorporated by reference as if set forth herein.

A variety of patterns may be formed using an electric discharge machine. Preferably a diamond pattern or a waffle pattern is formed on either inner surface 333 of ring 200 or outer surface 331 of head 325 of bone screw 125.

In another embodiment, inner surface 333 of ring 200 and/or outer surface 321 of head 325 of bone screw 125 may be textured by the use of a shot peening process. A shot peening process for forming a textured surface is described in U.S. Pat. No. 5,526,664 to Vetter which is incorporated by reference as if set forth herein. In general, a shot peening process involves propelling a stream of hardened balls, typically made of steel, at a relatively high velocity at a surface. To create a pattern upon an area of the surface the stream is typically moved about the surface. The speed by which the stream is moved about the surface tends to determine the type of textured surface formed.

Preferably, the stream is moved such that a pattern resulting in a textured surface having ridges and valleys is formed on inner surface 333 of ring 200 and outer surface 331 of head 325 of bone screw 125. When the textured inner surface 331 of ring 200 and the textured head 325 of bone screw 125 are coupled together the ridges and valleys may interact with each other to provide additional resistance to movement in either a longitudinal direction or a direction perpendicular to the longitudinal axis.

In another embodiment, the textured surface may be produced by embedding sharp hardened particles in the surface. A method for embedding sharp hardened particles in a metal surface is described in U.S. Pat. No. 4,768,787 to Shira which is incorporated by reference as if set forth herein. The method of Shira involves using a laser or other high energy source to heat the surface such that the surface melts in selected areas. Just before the molten area re-solidifies, a stream of abrasive particles is directed to the area. In this manner some of the particles tend to become embedded within the molten surface. The particles typically have a number of sharp edges that protrude from the surface after the particles have been embedded within the surface.

Any of the above methods of texturing may be used in combination with another method. For example, outer surface 331 of head 325 of bone screw 125 may be textured using a pattern of grooves. Inner surface of ring 200, however, may be textured using an electrical discharge method. When coupled together the textured surfaces of bone screw 125 and ring 200 may interact with each other to provide additional resistance to movement in either a longitudinal direction or a direction perpendicular to the longitudinal axis.

Textured surfaces may also be formed on any of the other surfaces of the plate system. The formation of textured surfaces preferably increases the frictional resistance between the various components of the plate system.

Figure 16:
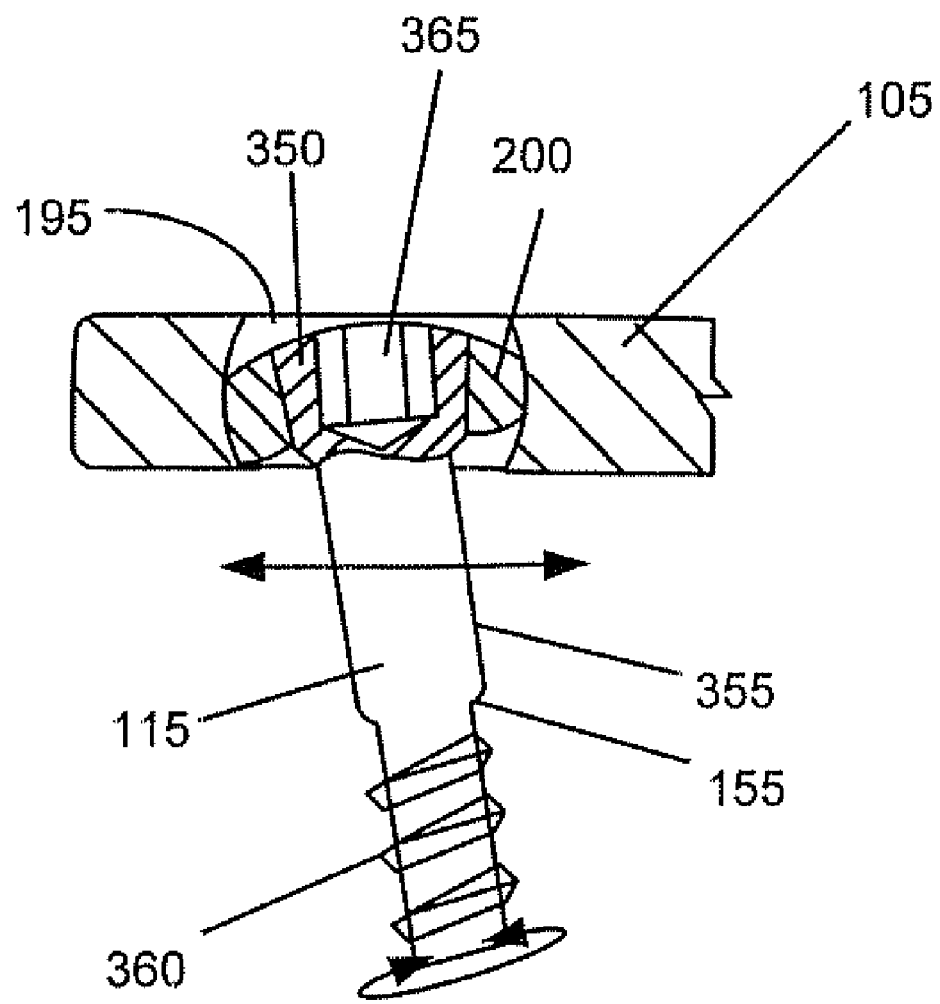
FIG. 16 is a diagrammatic representation of one embodiment of an attachment member coupled to a plate.

While FIGS. 6-15 generally describe embodiments of attaching bone screws 125 to plate 105, attachment member 115 can be similarly coupled to plate 105, FIG. 16 is a diagrammatic representation illustrating that similar attachment mechanisms can be used to couple attachment member 115 to plate 105 FIG. 16 depicts a cross-sectional view of an embodiment of hole 195 in which attachment member 115 is disposed. Hole 195 is preferably substantially spherical in shape so that a head 350 of attachment member 115 may be rotated and moved to various positions within hole 195. Ring 200 is preferably sized to fit into hole 195 between plate 105 and head 350. The outer surface of ring 200 is preferably curved to permit movement of the ring within hole 195. The combination of ring 200 and hole 195 is like that of a ball and socket since ring 200 may be rotated both horizontally and vertically in clockwise and counterclockwise directions within hole 195. Ring 200 may also be rotated in directions that are angled away from the horizontal and vertical directions. In FIG. 16, ring 200 at least partially surrounds head 350 of attachment member 115 which is positioned within hole 195. A shank of attachment member 115 preferably has threading 360 to allow attachment member 115 to screw into a corresponding cavity of interbody device 110 and a shoulder 155 to abut a countersunk surface 150 of the insert interbody (as shown in FIG. 1). Head 350 preferably includes a cavity 365 that extends from the top of the head to an inner portion of the head. Cavity 365 may be shaped to receive the end of any fastening device e.g., a socket wrench that may be used to turn attachment member 115.

The inner surface of ring 200 and the outer surface of head 350 are preferably tapered and shaped to mate with each other. The bottom portion of head 350 is preferably smaller than the upper portion of ring 200. As attachment member 115 is screwed into the interbody, head 350 preferably applies a radial force to ring 200, thereby causing the ring to expand within the hole and increase the size of the ring's gap. An interference fit may form between head 350, ring 200, and plate 105 in which these elements fit so tightly together that they obstruct the movements of each other. The hoop stress of ring 200 on head 350 may fixedly attach attachment member 115 to plate 105. Attachment member 115 shows that attachment member 115 may be obliquely angulated with respect to plate 105. Attachment member 115 may be positioned where it is at an angle ranging from 0 to 15 degrees or greater. The arrows of FIG. 16 illustrate that attachment member 115 can rotate clockwise and counter clockwise and angle to the left and right. Additionally, attachment member 115 can angle into or out of the paper. Thus, attachment member 115 can rotate in three dimensions relative to plate 105. While a particular embodiment of attachment member 115 and ring 200 are illustrated for coupling attachment member 115 to plate 105, other embodiments can be used including, but not limited to, those described in conjunction with FIGS. 6-15.

FIG. 17 illustrates another embodiment of a system that allows attachment member 115 to move relative to plate 105. In the embodiment of FIG. 17, plate includes a channel 370 into which a head portion of attachment member 115 fits. Channel 370 allows attachment member 115 to slide up and down. Optionally, attachment member 115 can be locked in place once a selected position is achieved. While channel 370 is shown as an elongated slot, channel 370 can have a variety of other shapes including, but not limited to, an "X" shape, "H" shape, "I" shape, "T" shape or other shape. According to one embodiment, attachment member 115 can be placed in channel 370 by angling attachment member 115 past a particular angle, through a keyhole feature or other mechanism.

FIGS. 18A and 18B are diagrammatic representations of example cross sections of channel 370 that allow attachment member 115 to be angled. In the example of FIG. 18A, head 350 is captured by the sidewalls of channel 370 in a manner that prevents attachment member 115 from falling out of channel 370, but still allows rotation. While head 350 is shown as flat, head 350 can be spherical or have another shape. Additionally, head 350 can include features that allow attachment member 115 to be rotated by a tool, such as an allen wrench, screwdriver or other tool. In the example of FIG. 18B, head 350 is generally spherical with a flange 375 or other feature that is captured by the sidewalls of channel 370 in a manner that allows attachment member 115 to be angled relative to plate 105. Head 350 can include features that allow attachment member 115 to be rotated by a tool, such as an allen wrench, screwdriver or other tool. In both of FIGS. 18A and 18B, attachment member can rotate clockwise/counterclockwise, left and right (as shown) and into and out of the page.

Figure 19:
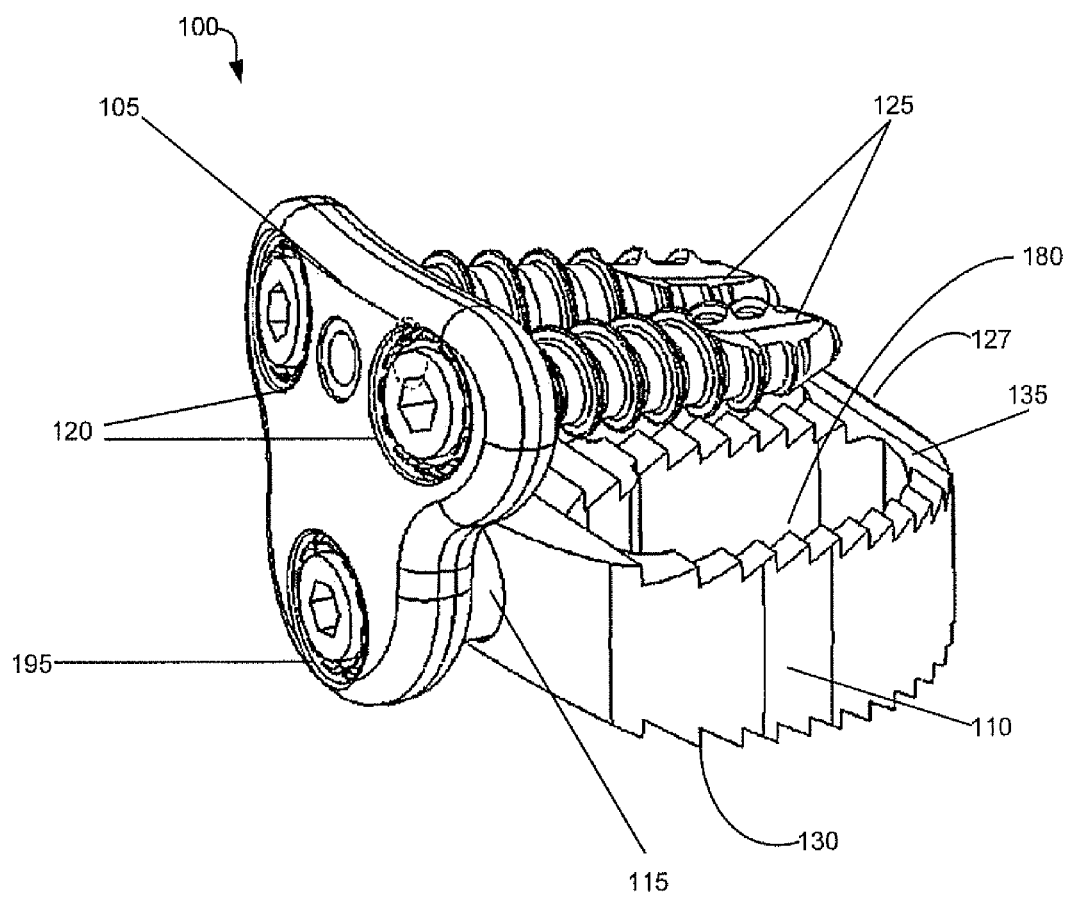
FIG. 19 is a diagrammatic representation of another embodiment of a spinal implant.

FIG. 19 is a diagrammatic representation illustrating an oblique view of another embodiment of implant 100, emphasizing surface 127 of interbody device 110 and showing features such as protrusions 135, discussed above. While shown as having a generally oblong shape, interbody device 110 can have a rectangular, square, circular or other shape. FIG. 19 further illustrates that interbody device 110 can include channels, such as channel 180, running from surface 127 to surface 130. While shown as having a substantial area compared to the overall area of interbody device 110 the channels can be relatively small and more numerous, not present at all or otherwise configured. The channels can allow bone to pass as bone growth occurs, thereby allowing the vertebrae to fuse together. Additionally, the channels can be packed with bone growth material. By way of example, but not limitation, the bone growth material can include autograft bone (such as bone from the patient's iliac crest), allograft bone, synthetic bone growth material or combinations thereof. FIG. 19 further illustrates holes 120 for fasteners to attach plate 105 to a single vertebra and hole 195 for attachment member 115. As discussed above, attachment member 115 and fasteners 125 can be coupled to plate 105 in a manner that allows attachment member 115 and fasteners 125 to rotate in multiple directions relative to plate 105.

During a procedure in which a disc has been fully or partially removed from the spine, the surgeon can assemble implant 100 external to the patient. Assembly can include selecting one or more of the appropriate plate 105, interbody device 110 and attachment member 115 to create an appropriately sized implant 100. In assembling implant 100, the surgeon can insert ring 200 and attachment member 115 into hole 195. The surgeon can then attach interbody device 110 to attachment member 115. The surgeon can then insert implant 100 into the body such that plate 105 abuts the one or more vertebrae and interbody device 110 is partially or fully inserted into the disc space. When interbody device 110 is in place, the surgeon can rotate plate 105 relative interbody device 110 in multiple dimensions to better align plate 105 with the one or more vertebrae to which it will be attached. The surgeon can then fasten plate 105 to the one or more vertebrae with bone screws 125 or other fasteners.

According to one embodiment, end plate 105 is prepared for surgical implantation by pre-positioning of rings 200 within holes 120 and 195. During the actual surgical procedure, holes may be drilled and tapped into the bones to which plate 105 is to be attached. Each of the screws 125 may be screwed into the bone holes while they are being positioned within their corresponding holes 120. Each pair of screws 125 may be positioned so that shanks of the screws are at oblique angles relative to the plate. The insertion force of each screw 125 into each ring 200 preferably causes the ring to exert a compressive force on the screw head, thereby fixably connecting the screws to plate 105.

In the previous example, implant 100 is fully assembled external to the patient. In another embodiment, the surgeon assembly plate 105 and attachment member 115 external to the patient but not yet couple interbody device 110 to attachment member 115. The surgeon can position interbody device 110 in the disc space and then insert attachment member 115 into the cavity of interbody device 110. Plate 105 can then be positioned relative to the one or more vertebrae to which it will be attached. Bone screws 125 can then fasten plate 105 in place. Again, in this example, rings 200 may be pre-positioned in holes 120 and 195.

Because plate 105 can rotate in multiple directions relative to interbody device 110, a surgeon can better position plate 105 relative to the spine. This can eliminate or substantially reduce the need to physically bend plate 105 to abut the vertebrae. Furthermore, the use of plate 105 prevents expulsion of interbody device 110 without the need for posterior side bone screws. Moreover, a surgeon can select the appropriate depth of insertion of interbody device 110 by selecting the appropriate attachment member 115 and/or interbody device 110.

While the present invention has been described with reference to particular embodiments, it should be understood that the embodiments are illustrative and that the scope of the invention is not limited to these embodiments. Many variations, modifications, additions and improvements to the embodiments described above are possible. It is contemplated that these variations, modifications, additions and improvements fall within the scope of the invention as detailed in the following claims.

What is claimed is:
1. A spinal implant comprising:
a plate for stabilizing the spine;

an interbody device defining a cavity opening to a first face facing the plate;

a ring sized to fit in a hole of the plate and having an outer surface curved to permit movement of the ring within the hole;

an attachment member for coupling the plate and the interbody device, the attachment member comprising:

a head having an outer surface shaped to mate with an inner surface of the ring; and a first portion for insertion in the cavity of the interbody device;

wherein the attachment member is part of the spinal implant and rotatable about at least three axes relative to the plate and is fixedly attachable to the plate by hoop stress of the ring on the head within the hole of the plate.

2. The spinal implant of claim 1, wherein the ring allows the angle of the attachment member to the plate to be adjusted.

3. The spinal implant of claim 2, wherein the ring at least partially surrounds the head.

4. The spinal implant of claim 1, wherein the cavity is a counterbore and the first portion of the attachment member is unthreaded.

5. The spinal implant of claim 1, wherein the first portion of the attachment member comprises a male threaded portion and the cavity comprises a female threaded portion.

6. The spinal implant of claim 5, wherein the cavity comprises a countersunk portion.

7. The spinal implant of claim 6, wherein the attachment member comprises a shoulder that abuts a surface of the countersunk portion.

8. The spinal implant of claim 1, wherein the attachment member comprises a stop that abuts a surface of the interbody device.

9. The spinal implant of claim 8, wherein the stop defines a desired depth of insertion of the interbody device between two vertebrae.

10. The spinal implant of claim 1, further comprising a plurality of fasteners for fastening the plate to at least one vertebra.

11. The spinal implant of claim 10, wherein each of the plurality of fasteners is rotatable about three axes relative to the plate via a corresponding ring movable within a corresponding hole in the plate.

12. A spinal implant method comprising:

selecting an attachment member;

coupling the attachment member to a plate configured to attach to at least one vertebra, wherein the attachment member is rotatable relative to the plate about at least three axes when coupled to the plate via a ring sized to fit in a hole of the plate and having an outer surface curved to permit movement of the ring within the hole; and inserting a first portion of the attachment member into a corresponding cavity in an interbody device;

wherein at least the attachment member is selected to achieve a desired minimum distance between the interbody device and the plate; and wherein the attachment member, the interbody device, and the plate form a spinal implant.

13. The spinal implant method of claim 12 comprising selecting the interbody device to achieve a desired angle of lordosis.

14. The method of claim 12, further comprising selecting the interbody device to achieve a desired separation between the two vertebrae.

15. The method of claim 12, further comprising selecting the interbody device in conjunction with the attachment member to achieve the desired minimum distance between the interbody device and the plate.

16. The method of claim 12, further comprising positioning a second portion of the attachment member in the hole in the plate.

17. The method of claim 16, further comprising placing the ring in the hole the plate and the second portion of the attachment member.

18. The method of claim 17, further comprising rotating the attachment member to cause the ring to move in the hole to adjust the angle of the attachment member.

19. The spinal implant of claim 17, wherein the second portion of the attachment member comprises the head.

20. The method of claim 12, wherein the first portion of the attachment member comprises smooth surfaces.

21. The method of claim 12, wherein the cavity comprises a countersunk portion open to a first face of the interbody device.

22. The method of claim 12, wherein the first portion of the attachment member comprises a male threaded portion and the cavity comprises a female threaded portion.

23. The method of claim 22, wherein the cavity comprises a countersunk portion.

24. The method of claim 23, wherein the attachment member comprises a shoulder that abuts a surface of the countersunk portion.

25. The method of claim 12, wherein the attachment member comprises a stop that abuts a surface of the interbody device.

26. The method of claim 12, further comprising:

inserting the interbody device in a space between two vertebrae;

rotating the plate relative to the interbody device through the ring between the plate and the attachment member to position the plate in a desired position;

fixedly attaching the attachment member to the plate by applying hoop stress of the ring on the head within the hole of the plate; and fastening the plate to at least one of the two vertebrae.

27. The method of claim 12, wherein the attachment member is selected from a surgical kit containing multiple attachment members configured to provide various minimum distances between the plate and the interbody device.

28. A spinal implant comprising:

a plate for stabilizing the spine;

an interbody device having a counterbore in a first face;

a ring sized to fit in a hole of the plate and having an outer surface curved to permit movement of the ring within the hole; and an attachment member for coupling the plate and the interbody device, the attachment member being part of the spinal implant and comprising:

a head having an outer surface shaped to mate with an inner surface of the ring; and a portion for insertion in the counterbore of the interbody device.

29. The spinal implant of claim 28, wherein the portion of the attachment member is unthreaded.

30. The spinal implant of claim 28, wherein the counterbore forms a portion of a cavity with an adjacent threaded section.

31. The spinal implant of claim 30, wherein the attachment member comprises a corresponding threaded section to engage the threaded section of the cavity.

32. The spinal implant of claim 31, wherein the attachment member comprises a shoulder that abuts a surface of the counterbore to limit the insertion distance of the attachment member into the cavity.

33. The spinal implant of claim 32, wherein the counterbore is a countersink.

34. The spinal implant of claim 28, wherein the attachment member comprises a stop that abuts a surface of the interbody device.

35. The spinal implant of claim 34, wherein the surface is the first face of the interbody device.

36. The spinal implant of claim 34, wherein the surface is a counterbore surface at least partially defining the counterbore.

37. A spinal implant comprising:
a plate for stabilizing the spine, wherein the plate has a first end and a second end;
an interbody device defining a cavity opening to a first face facing the plate; and
an attachment member for coupling the plate and the interbody device, the attachment member comprising:
a head portion having an outer surface shaped to mate with an inner surface of a hole in the plate, wherein the hole is between the first end and the second end of the plate; and
a first portion for insertion in the cavity of the interbody device;
wherein the attachment member is part of the spinal implant, is rotatable relative to the plate, and is fixedly attachable to the plate via the head portion.

38. The spinal implant of claim 37, wherein the plate has a first fastener hole at the first end and a second fastener hole at the second end.

39. The spinal implant of claim 37, wherein the interbody device comprises a plurality of protrusions.

40. The spinal implant of claim 37, wherein the head portion of the attachment member is sized to fit entirely or substantially entirely within the hole of the plate.

41. The spinal implant of claim 37, wherein the outer surface of the head portion of the attachment member is curved to permit movement of the head portion within the hole in the plate.

42. A method comprising:
selecting an attachment member, the attachment member having a head portion and a first portion;
coupling the attachment member to a plate via a hole in the plate, wherein the plate has a first end and a second end, wherein the hole is between the first end and the second end of the plate, wherein the attachment member is rotatable relative to the plate when coupled to the plate via the head portion; and
inserting the first portion of the attachment member into a cavity in an interbody device;
wherein at least the attachment member is selected to achieve a desired minimum distance between the interbody device and the plate; and
wherein the attachment member, the interbody device, and the plate form a spinal implant.

43. The method of claim 42, wherein the plate has a first fastener hole at the first end and a second fastener hole at the second end.

44. The method of claim 42, wherein the interbody device comprises a plurality of protrusions.

45. The method of claim 42, wherein the head portion of the attachment member is sized to fit entirely or substantially entirely within the hole of the plate.

46. The method of claim 42, wherein an outer surface of the head portion of the attachment member is curved to permit movement of the head portion within the hole in the plate.

* * * * *